(12) United States Patent
Lepore (10) Patent No.: US 6,345,449 B1
(45) Date of Patent: Feb. 12, 2002

(54) METHOD OF STERILIZATION OF MUSICAL WIND INSTRUMENTS

(76) Inventor: Lorenzo Lepore, 117 Whitney Rd., Medford, MA (US) 02155

( * ) Notice: Subject to any disclaimer, the term of this patent is extended or adjusted under 35 U.S.C. 154(b) by 0 days.

(21) Appl. No.: 09/635,342

(22) Filed: Aug. 9, 2000

Related U.S. Application Data (60) Provisional application No. 60/147,887, filed on Aug. 9, 1999.

(51) Int. Cl.$^7$ .................................................. F26B 7/00
(52) U.S. Cl. ............................ 34/389; 34/380; 34/437; 34/516; 84/380 R; 84/458; 422/28; 422/34; 422/294
(58) Field of Search ........................... 34/380, 389, 390, 34/437, 467, 516, 521; 84/380 R, 453, 458; 422/28, 33, 34, 291, 294, 295

(56) References Cited

U.S. PATENT DOCUMENTS

| | | | |
|---|---|---|---|
| 3,476,506 A | 11/1969 | Andersen et al. | 422/294 |
| 4,107,976 A | 8/1978 | Andersen et al. | 73/52 |
| 4,145,186 A | 3/1979 | Andersen | 436/1 |
| 4,937,046 A | 6/1990 | Andersen et al. | 422/34 |
| 5,060,336 A * | 10/1991 | LaLonda | 15/104.1 R |
| 5,082,636 A | 1/1992 | Andersen | 422/294 |
| 5,118,471 A | 6/1992 | Andersen et al. | 422/34 |
| 5,135,715 A | 8/1992 | Andersen | 422/28 |
| 5,160,700 A | 11/1992 | Andersen et al. | 422/34 |
| 5,227,132 A | 7/1993 | Andersen et al. | 422/2 |
| 5,241,803 A | 9/1993 | Griffin | 53/425 |
| 5,302,358 A | 4/1994 | Anderson et al. | 422/305 |
| 5,524,357 A * | 6/1996 | Crabb | 34/202 |
| 6,005,179 A * | 12/1999 | Currie | 84/453 |
| 6,134,806 A * | 10/2000 | Dhaemers | 34/404 |

OTHER PUBLICATIONS

Zory Glaser, PhD –The Future of Ethylene Oxide as a Medical Device Sterilant in Healthcare Facilities –Infection Control Today –April 1998.

David L. Lewis et al. –Cross–Contamination Potential with Dental Equipment –The Lancet –vol. 340; Nov. 21, 1992.

Elevating Standards of Infection Control –*www.anpro.com* Copyright© 1999 Anderson Products.

Andersen, L. et al. –An Introduction to Gas–Diffusion Sterilization (May 97) Device & Diagnostic Industry,, pp. 137–150.

Mayworm, D. –100% EO Processing: Another Alternative (Aug. 96) Infection Control & Sterilization Technology, vol. 2, No. 8.

Andersen, Lintott, Hu. –Outsourcing Sterile Reprocessing (Jul. 97) Infection Control & Sterilization Technology, pp. 24–32.

(List continued on next page.)

Primary Examiner—Pamela Wilson
(74) Attorney, Agent, or Firm—Mintz, Levin, Cohn, Ferris, Glovsky and Popeo, P.C.

(57) ABSTRACT

A method of sterilizing musical instruments is provided. More particularly, a method of sterilizing musical wind instruments is provided for sterilizing, or at least sanitizing, musical wind instruments without damaging or degrading components of such instruments constructed of cloth, wood, plastic, rubber or fibrous materials. The method of the invention uses a gas diffusion process and a gas sterilant, such as ethylene oxide. A musical wind instrument is placed in a gas diffusion bag and a sterilizing atmosphere is created within the gas diffusion bag by releasing ethylene oxide into the gas diffusion bag at a sufficient concentration to act as a sterilant. Ethylene oxide is heated to an appropriate temperature and maintained at such temperature for a sufficient time to achieve sterilization, or at least sanitization, of the musical wind instrument contained therein.

16 Claims, 4 Drawing Sheets

OTHER PUBLICATIONS

Waldron, E. –Niché Players Can Thrive in the Global Market (Nov. 97) Medical Device & Diagnostic Industry.

Sordellini, Paul J –Speeding EtO–Sterilized Products to Market with Parametric Release Medical Device & Diagnostic Industry (Feb. 97).

Mayworm, Dan –Low Temperature Sterilization Revisited –Infection Control Sterilization Technology –February 1998 –p. 22.

Anprolene AN7D & E Sterilizers Brochure/Instruction Manual.

* cited by examiner

METHOD OF STERILIZATION OF MUSICAL WIND INSTRUMENTS

CLAIM OF PRIORITY

This application claims priority under 35 U.S.C. § 119(e) to United States provisional patent application Ser. No. 60/147,887, filed on Aug. 9, 1999, incorporated herein by reference.

FIELD OF THE INVENTION

The present invention provides a method of sterilizing musical wind instruments. More particularly, the present invention provides a sterilization method using a gas diffusion process and a gas sterilant, such as ethylene oxide, to sterilize, or at least sanitize, musical wind instruments that are shared by two or more persons.

BACKGROUND OF THE INVENTION

Playing musical instruments is a very popular activity in the United States and throughout the world. Musical instruments generally fall into three classes: string instruments, percussion instruments and wind instruments. The string instruments, i.e. violins, guitars, cellos and the like, produce musical tones by bowing or plucking strings which vibrate in audible frequencies. The percussion instruments, i.e. drums, gongs, cymbals, tympani and the like, produce sounds by providing a surface which is struck with a stick, mallet or similar object. One hybrid instrument, the piano, produces tones using strings which are struck by padded hammers that are controlled using a keyboard. Finally, the wind instruments produce musical tones when air is blown through them or across openings in them.

The wind instruments are classifying in two main categories. Brass instruments, such as trumpets, French horns, trombones, tubas and the like, are usually constructed of metals and include a bell shaped mouthpiece that the musician places against his or her lips. Woodwinds, such as clarinets, saxophones, oboes, bassoons and the like are usually constructed of a variety of materials and include a single or double reed which is placed partially in the musician's mouth. One family of woodwinds, the flutes, do not include a reed, but rather have an aperture called an embouchure which the musician blows across to produce a musical tone.

A wide variety of materials is employed in constructing wind instruments. While the brass instruments are constructed primarily of metals, woodwinds tend to comprise a combination of woods, metals, plastics, rubbers and fibrous materials such as cotton. In fact, some flutes even use fish scales in the design of pads which cover and expose various keyholes. Since the wind instruments are played by blowing into them, it is natural that some of the musician's body fluids, including blood elements, saliva and water vapor, will accumulate in their interiors. Instruments that include curved portions often include a mechanism, called a spit-valve, that can be opened to allow accumulated fluids to be drained from the instrument.

Most serious musicians own their instruments and treat them as very personal objects. That notwithstanding, however, many beginning music students, particularly those in elementary and secondary schools, use instruments which they have borrowed from the institution in which they receive their musical training. Typically, a student may rent an instrument for a semester or a school year, returning it upon completion of the rental period. In many locations, the practice is to store the returned instrument until the next musician seeking such an instrument rents it. There is nothing to guarantee that each student will receive the same instrument from rental term to rental term.

As a result of these practices, student musicians often obtain instruments that have been rented and used by others. This raises sanitary issues, however, because at present, little if anything is done to clean or sanitize instruments between rentals. Thus, while the exterior of the instruments may receive a polish, the interior remains coated with dried saliva and exhaled water vapor from the prior user. This raises potential problems since the interior of wind instruments, particularly when damp, can form an excellent environment for the growth of infectious microbes, such as bacteria or viruses, which can cause illness when ingested or inhaled. The medical model of universal precautions mandates that all patients and the devices used in their treatment (especially when bodily fluid contamination is included) be viewed as potentially infectious. Applying these precautions to musical wind instruments makes good sense, since musical wind instruments, and particularly their interiors, are repeatedly contacted with bodily fluids as a natural result of the musician playing the instrument.

Sterilization of instruments raises several difficult practical and technical problems. For example, on the practical side, any sterilization must be relatively affordable, simple and not overly time-consuming. On the technical side, the sterilization of items constructed of a variety of materials including organic materials such as woods and cotton is a challenge. Of course, any sterilization method employed must be one which causes virtually no physical damage to the instrument. This is an issue because many known sterilizing agents, such as ultraviolet radiation, are known to degrade organic materials such as wood.

Thus, a need exists for affordable and efficient methods which allow the sterilization, or at the very least, the sanitization, of musical wind instruments. These methods must also be such that they do not damage the musical wind instruments during the sterilization process.

SUMMARY OF THE INVENTION

The invention provides a method of sterilizing a musical wind instrument using a gas diffusion process. In a first embodiment of the invention, the method of sterilization comprises steps of placing the musical instrument in an open, sealable diffusion bag, evacuating air from the diffusion bag, sealing the diffusion bag to achieve a leak-proof seal, placing the diffusion bag in a chamber of a sterilizer equipped with an exhaust ventilation system, creating a sterilizing atmosphere within the diffusion bag by introducing a gas sterilant, such as ethylene oxide or propylene oxide, into the interior of the diffusion bag, heating the gas sterilant to an appropriate temperature, maintaining the temperature of the gas sterilant for a sufficient time to achieve sterilization, or at least sanitization, of the musical wind instrument, and removing the diffusion bag from the sterilizer with the musical wind instrument contained therein.

In a version of the first embodiment, the sterilizing atmosphere is created within the interior of the gas diffusion bag by introducing a unit dose of ethylene oxide into the interior of the diffusion bag by a remotely-activated cartridge that releases 100% ethylene oxide gas, at a concentration of about 600 mg/l to about 750 mg/l, into the diffusion bag upon activation by an external trigger. The unit dose of ethylene oxide is measured in relation to a volume of the interior of the gas diffusion bag. The ethylene oxide gas is heated to an appropriate sterilization temperature of about 45° C. to about 55° C., and maintained at such temperature for a sufficient time of about 4 to about 16 hours to achieve sterilization. After completion of sterilization, residual ethylene oxide gas molecules absorbed by gas-absorbent materials of the musical wind instrument and contained within the diffusion bag and the sterilization chamber are substantially removed by purging and exhausting ethylene oxide gas molecules for a sufficient time of about 16 to 24 hours to the outside atmosphere.

The gas diffusion bag is constructed of a suitable material that is tear-resistant and allows ethylene oxide to diffuse outwardly from the interior of the diffusion bag, such as, although not limited to, low density polyethylene.

In a second embodiment of the invention, the ethylene oxide gas is introduced into the interior of the gas diffusion bag to create the sterilizing atmosphere by a gas cylinder injector system. The gas cylinder injector system contains a gas cylinder containing 100% ethylene oxide and is equipped with an adjustably connected injector. The injector is inserted into the gas diffusion bag, withdraws or evacuates air from the diffusion bag, and injects ethylene oxide gas into the gas diffusion bag. The gas diffusion bag is then sealed to achieve a leak-proof seal. The injection of ethylene oxide into individual the gas diffusion bag proceeds within operation of a high-volume exhaust ventilation system that exhausts diffusing gas molecules to the outside atmospheres. The gas diffusion bag is thereafter placed either in the sterilization chamber of the sterilizer or into a temperature-controlled chamber or room. The gas cylinder injector system is conducive for use with multiple lots of individual gas diffusion bags.

In a third embodiment of the invention, the musical wind instrument is contained in a musical instrument carrying case and placed within the interior of the gas diffusion bag for sterilization. During the sterilization process, ethylene oxide gas molecules diffuse through the instrument carrying case and contact the musical wind instrument contained therein.

In a fourth embodiment of the invention, the sterilizing atmosphere is provided by a standard ethylene oxide sterilizer, such as an ethylene oxide sterilizer used by hospitals to sterilize medical instruments, wherein the gas diffusion bag is placed within the sterilization chamber of the ethylene oxide sterilizer and ethylene oxide is released into the sterilization chamber. Upon heating ethylene oxide to an appropriate temperature, ethylene oxide gas molecules diffuse through a polyethylene member incorporated with a wall of the gas diffusion bag. Ethylene oxide gas molecules circulate throughout the gas diffusion bag, contacting the musical wind instrument contained therein.

BRIEF DESCRIPTION OF THE DRAWINGS

For a better understanding of the invention, reference is made to the drawings which are incorporated herein by reference and in which.

DETAILED DESCRIPTION OF THE INVENTION

Illustrative embodiments of the invention described below provide a method of sterilizing musical wind instruments by a gas diffusion process using a gas sterilant. Those skilled in the art will appreciate, however, that embodiments in accordance with the invention are not limited to sterilizing musical wind instruments, but, rather, may be used to sterilize other types of musical instruments, including string musical instruments.

Embodiments of the invention will be described below with reference to FIGS. 1–4 which are presented herein for the purpose of illustrating embodiments and are not intended to limit the scope of the invention. The terms sterile, sterilize, sterilized, sterilizing, sterilizer and sterilization as used herein refer to processes, conditions, states or equipment for achieving at least the sanitization of musical instruments, wherein musical wind instruments are at least sanitary or free from infectious microbes and other elements that cause illness or endanger health.

Figure 1:
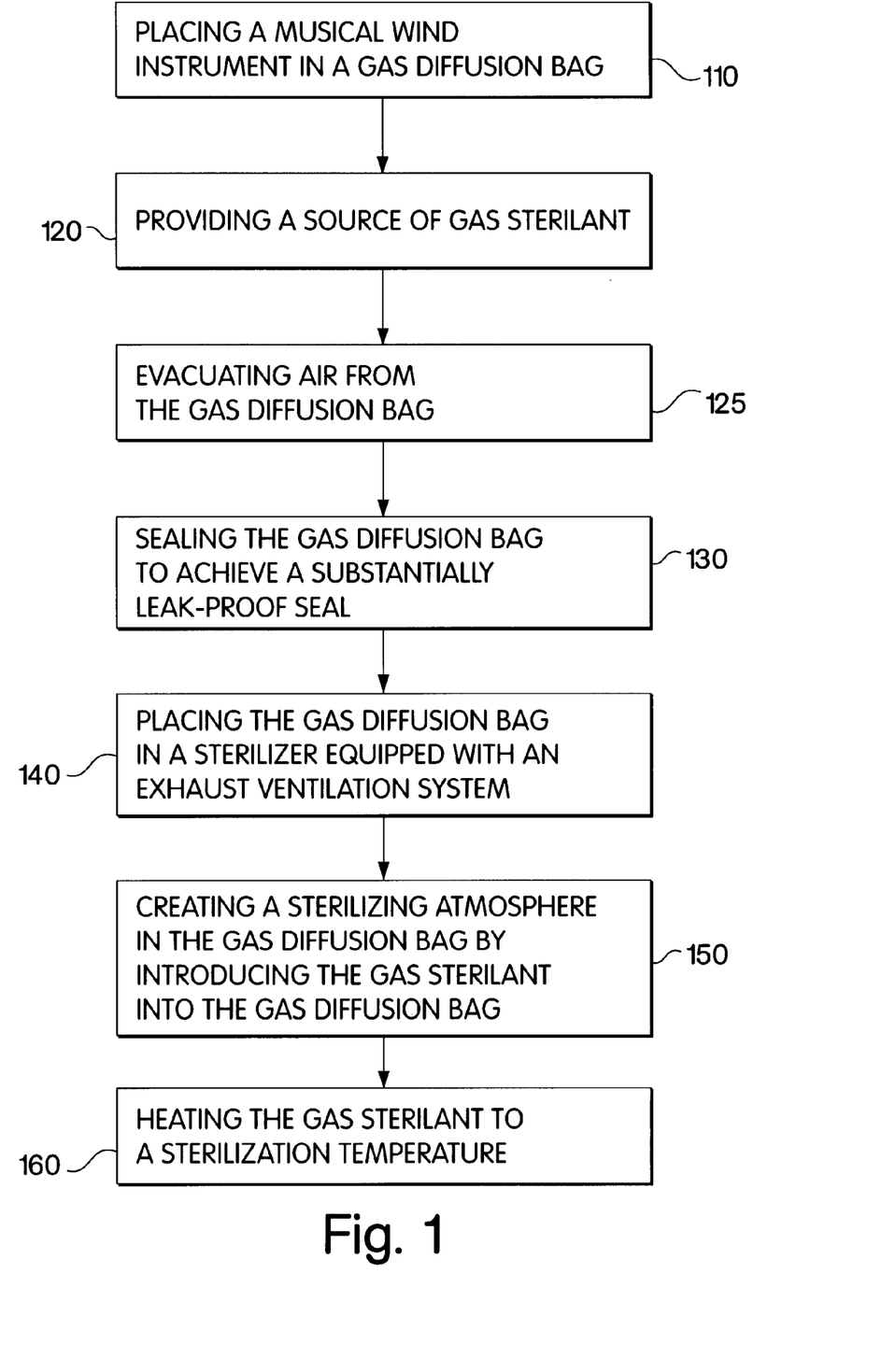
FIG. 1 is a flow diagram illustrating a first embodiment of a method of the invention.

Referring to FIG. 1, a first embodiment of the invention provides a method of sterilizing a musical wind instrument by a gas diffusion process including steps of placing the instrument in a gas diffusion bag in step 110; providing a source of a gas sterilant, such as, although not limited to, ethylene oxide or propylene oxide, in step 120; evacuating air from the gas diffusion bag in step 125; sealing the gas diffusion bag in step 130 to form a substantially leak-proof seal; placing the gas diffusion bag in a sterilizer equipped with an exhaust ventilation system in step 140; creating a sterilizing atmosphere in the gas diffusion bag by introducing the gas sterilant into the gas diffusion bag in step 150; and heating the gas sterilant to a sterilization temperature in step 160.

Figure 2:
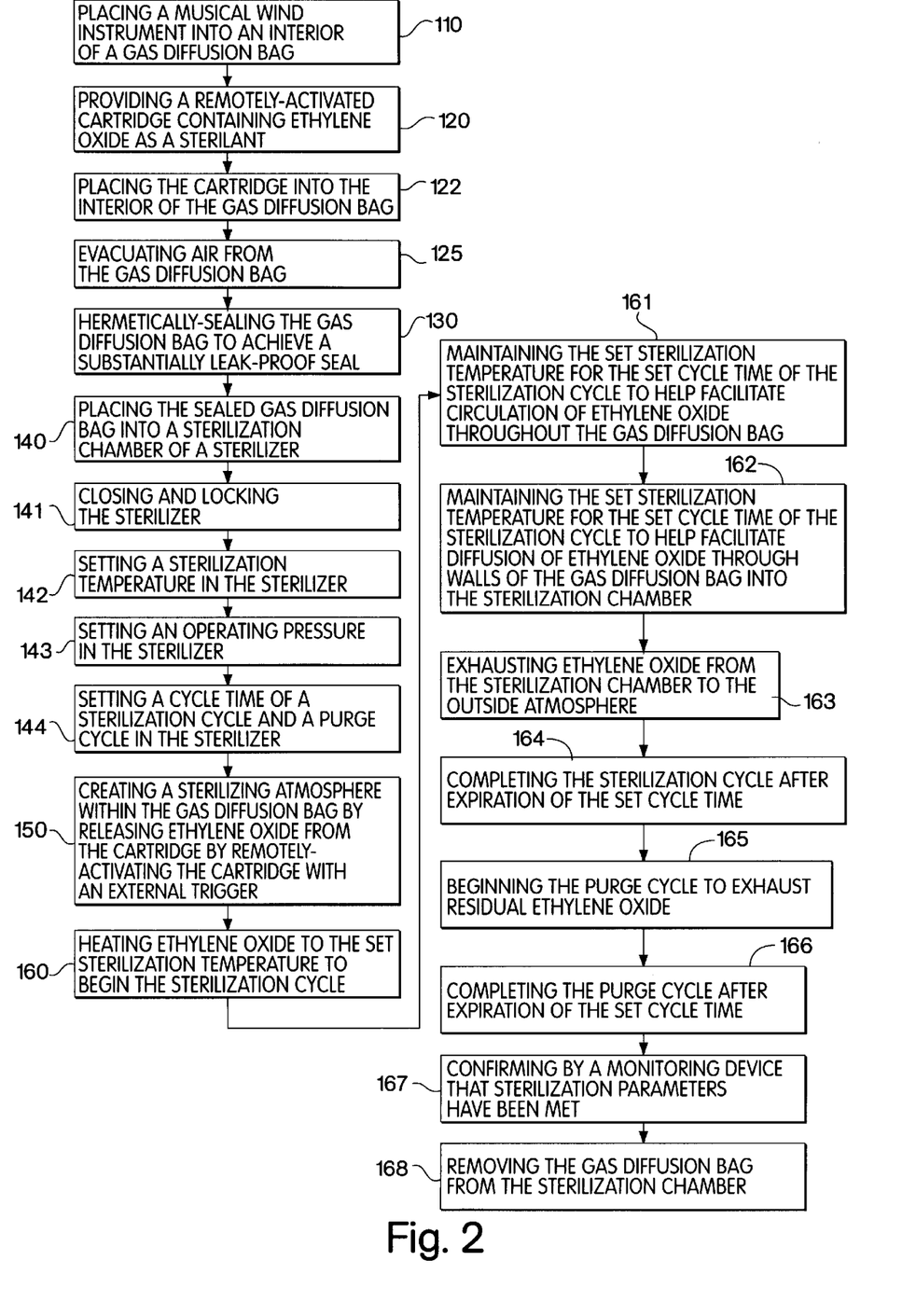
FIG. 2 is a flow diagram illustrating another version of the first embodiment.

Referring to FIG. 2, a version of the first embodiment of the method of the invention employs ethylene oxide as the gas sterilant and includes in step 110 placing the musical wind instrument into an interior of the gas diffusion bag, which is sized to accommodate the instrument and to provide sufficient interior volume for adequate circulation of ethylene oxide throughout the diffusion bag.

A source of ethylene oxide is provided in step 120 and includes a remotely-activated cartridge, which contains a measured unit dose of 100% ethylene oxide at a concentration of about 600 mg/l to about 750 mg/l. The quantity of the measured unit dose of ethylene oxide is calculated in relation to the size or volume of the gas diffusion bag, rather than the volume of a sterilization chamber of the sterilizer. Measuring unit doses of ethylene oxide according to the size or volume of the gas diffusion bag helps facilitate economy in the use of ethylene oxide as a sterilant by avoiding waste, while ensuring that the parameters of sterilization are met. In addition, the flexibility of the gas diffusion process used in the method of the invention allows use of ethylene oxide to be based upon the actual musical wind instrument to be sterilized rather than the volume of the sterilization chamber.

The cartridge is placed directly into the interior of the gas diffusion bag in step 122 together with the musical wind instrument to be sterilized. Air is evacuated from the gas diffusion bag in step 125. The gas diffusion bag is thereafter hermetically sealed, or sealed by other comparable methods well known in the art, in step 130 to achieve a substantially leak-proof seal. The sealed gas diffusion bag is subsequently placed in a sterilization chamber of the sterilizer in step 140. A door of the sterilizer is closed and locked in step 141.

In step 142, the sterilization temperature is set in the sterilizer. In addition, in step 143, a pressure under which the sterilizer operates is set, and, in step 144, cycle times of a sterilization cycle and a purge cycle are set in the sterilizer. Sterilization temperature is about 45° C. to about 55° C., and preferably about 50° C. The sterilization cycle operates for about 4 hours to about 16 hours at a pressure of about 0 to about 1 inch vac. The purge cycle operates for about 12 hours to about 24 hours. The cycle times of the sterilization cycle and the purge cycle depend upon the type of musical instrument to be sterilized and the materials with which the musical instrument is constructed. For example, musical instruments with highly detailed structures and intricate designs would require relatively longer sterilization cycles than musical instruments of simpler structures and designs in order to ensure a sufficient amount of the gas sterilant circulates or penetrates into the musical instruments and contacts substantially all surfaces of the musical instruments. In addition, various materials used to construct components of musical instruments, such as cloth, woods, plastics, rubbers and fibrous materials, are gas absorbent materials that require relatively shorter or longer purge cycles for the gas sterilant absorbed by such materials to be substantially diffused or purged from the materials after the sterilization cycle is complete.

In step 150, ethylene oxide is subsequently introduced into the gas diffusion bag to create the sterilizing atmosphere. The cartridge is remotely activated and opened to release ethylene oxide into the gas diffusion bag by pressing a trigger located exterior to the sterilizer. Ethylene oxide gas is heated to the set sterilization temperature in step 160 to begin the sterilization cycle. As ethylene oxide is released from the cartridge, ethylene oxide gas molecules permeate throughout the gas diffusion bag. Kinetic energy of the heated ethylene oxide gas causes the gas molecules to spread out by their own velocity into substantially every cubic centimeter of the interior volume of the gas diffusion bag. Ethylene oxide circulates around and penetrates into the musical wind instrument contained within the gas diffusion bag. Ethylene oxide kills microbes on substantially all surfaces of the musical wind instrument that are contacted by circulating ethylene oxide gas molecules without damaging or degrading components of the musical wind instrument, particularly components constructed of cloth, wood, cloth, plastic or rubber. The elevated sterilization temperature maintained throughout the set cycle time of the sterilization cycle, as described below in steps 161 and 162, maintains the kinetic energy of the ethylene oxide gas, which helps to facilitate the circulating and penetrating action of the ethylene oxide gas molecules in the gas diffusion bag.

As the concentration of ethylene oxide gas molecules increases inside the gas diffusion bag by release of gas molecules from the cartridge, ethylene oxide gas molecules circulate throughout the gas diffusion bag and gradually diffuse through walls of the bag into the sterilization chamber, as long as the set sterilization temperature is maintained in steps 161 and 162. The ethylene oxide gas molecules which are diffused into the sterilization chamber are exhausted to the outside atmosphere by an exhaust ventilation system of the sterilizer in step 163. More ethylene oxide gas molecules are released into the gas diffusion bag from the cartridge than are diffused from the gas diffusion bag into the sterilization chamber during initial hours of the sterilization cycle. Eventually, during the course of the sterilization cycle, the release of gas molecules and diffusion of gas molecules from the gas diffusion bag are about equal. Ethylene oxide is finally depleted from the cartridge to exhaust the source of the ethylene oxide. Ethylene oxide gas molecules continue to diffuse into the sterilization chamber for the remainder of the sterilization cycle.

The sterilization cycle is complete after the expiration of the set cycle time of at least about 4 hours in step 164. The amount of residual ethylene oxide gas molecules inside the gas diffusion bag and the sterilization chamber is small. The purge cycle begins in step 165 for the set cycle time of at least about 16 hours to remove and exhaust all remaining ethylene oxide gas molecules from the musical wind instrument, the gas diffusion bag and the sterilization chamber to the outside atmosphere prior to opening the sterilizer. The purge cycle is complete at the expiration of the set cycle time in step 166.

After completion of the purge cycle, monitoring devices or systems, such as biological and chemical indicators well known to those skilled in the art, are used in step 167 to confirm if the sterilization parameters have been met. If sterilization parameters have been met, the gas diffusion bag containing the sterile musical wind instrument is removed from the sterilization chamber in step 168.

The gas diffusion bag is thereafter used to store and transport the musical wind instrument in a sterilized state, thereby maintaining sterility of the instrument until such time as the end-user wishes to remove the instrument from the diffusion bag for use. New and used musical wind instruments may be similarly sterilized by the method of the invention. In addition, the sterilized musical wind instrument is provided to an end-user in the gas diffusion bag to demonstrate sterility of the instrument has been maintained during its storage and distribution. New musical wind instruments, upon completion of manufacture, may be factory-sterilized by the method of the invention prior to shipment to distributors, retail outlets and other end-users. In addition, used musical wind instruments may be sterilized by the method of the invention prior to transfer of musical wind instruments from previous end-users to new endusers. The sterilization method of the invention substantially reduces the potential of exposure of new end-users to infectious microbes, such as bacteria and viruses, residing in musical wind instruments that cause illness when ingested or inhaled. In addition, the method of the invention substantially reduces the possibility of spreading infectious microbes among the numerous users of a used musical wind instrument during its useful lifetime.

The gas diffusion bag is constructed of a suitable material that is tear-resistant and porous to ethylene oxide gas, such as, although not limited to, low density polyethylene. For example, polyethylene gas diffusion bags available from Andersen Products, Inc. of Haw River, N.C., are suitable diffusion bags for sterilization of musical wind instruments according to the method of the invention. Although such gas diffusion bags are tear-resistant, should a leak in the diffusion bag result, the leak is not critical to the method of the invention due to the negative air pressure that is established within the sterilizer during the sterilization and purge cycles. The negative air pressure in the sterilization chamber draws off ethylene oxide gas molecules and exhausts the gas molecules through the sterilizer ventilation system. The sterilizer, in effect, acts as an exhaust hood to evacuate diffusing ethylene oxide gas molecules, thereby promoting safety in the use of ethylene oxide as a gas sterilant.

In addition, the sterilizer and ethylene oxide cartridges described above, as well as other related equipment required to execute the sterilization method of the invention, are commercially available from a number of sources, including Andersen Products, Inc. of Haw River, N.C.

Figure 3:
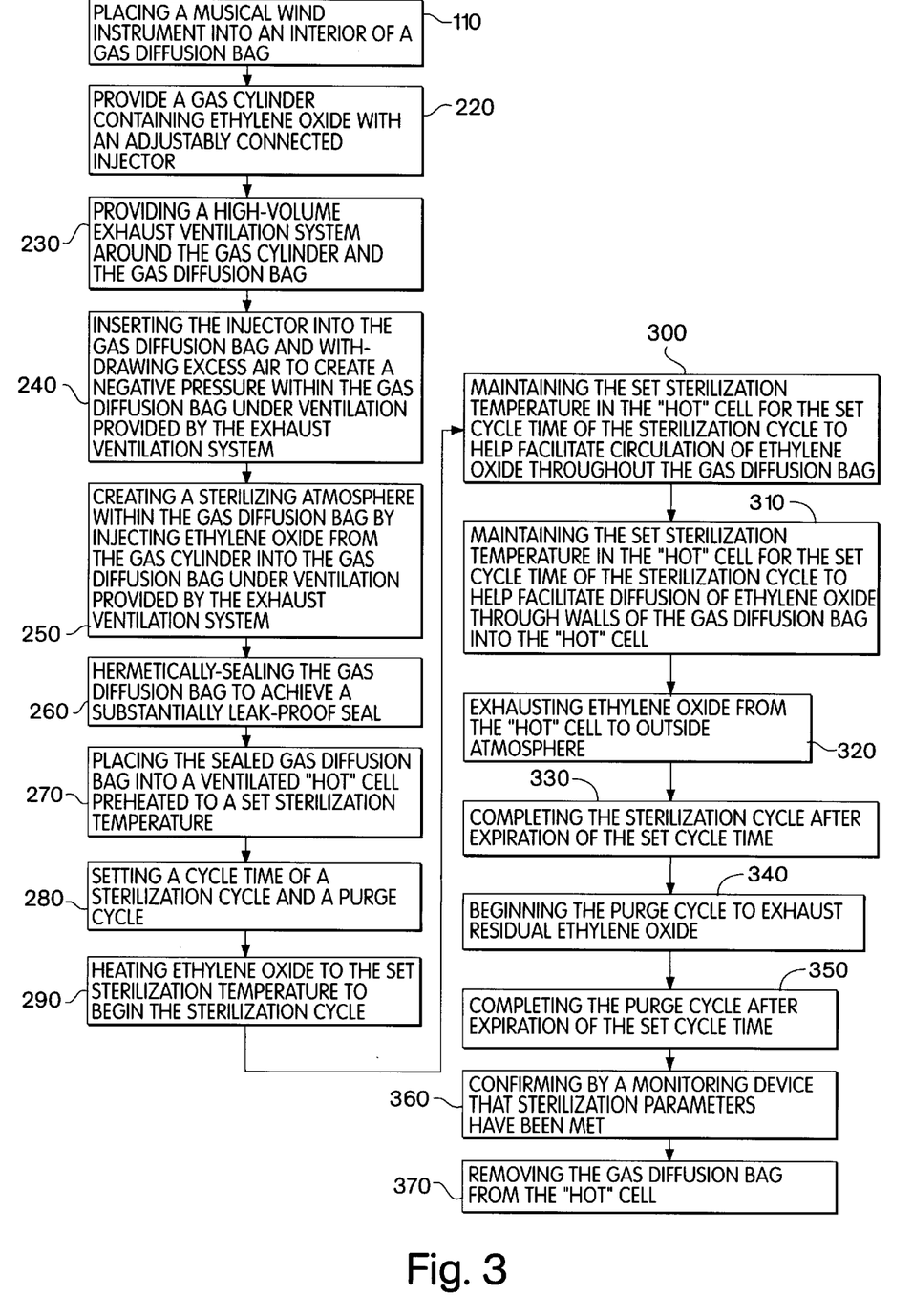
FIG. 3 is a flow diagram illustrating a second embodiment of the method of the invention.

Referring to FIG. 3, a second embodiment of the method of the invention includes creating the sterilizing atmosphere within the gas diffusion bag by introducing ethylene oxide into the gas diffusion bag with a gas cylinder injector system. The gas cylinder injector system injects a measured unit dose of ethylene oxide from a gas cylinder into the gas diffusion bag. The gas cylinder injector system is provided in step 220 and includes a gas cylinder with an injector adjustably connected to the gas cylinder for injecting ethylene oxide gas into individual diffusion bags. In step 230, a high-volume exhaust ventilation system is provided around the gas cylinder injector system and the gas diffusion bag to protect an operator of the gas cylinder injector from diffusing ethylene oxide gas during injection of ethylene oxide into the gas diffusion bag. The injector is inserted into the gas diffusion bag and withdraws excess air from the gas diffusion bag in step 240, under ventilation provided by the exhaust ventilation system, thereby creating a negative pressure within the gas diffusion bag. The injector subsequently injects a measured unit dose of ethylene oxide from the gas cylinder into the gas diffusion bag in step 250, creating a sterilizing atmosphere within the gas diffusion bag. Thereafter, in step 260, the gas diffusion bag is sealed, either hermetically or by other methods well known in the art, to achieve a substantially leak-proof seal. The gas diffusion bag is then placed in a "hot" cell in step 270, such as a preheated, ventilated chamber or room, in which the sterilization temperature is maintained and the sterilization cycle proceeds. Rather than relying upon individual cartridges of ethylene oxide inserted into each gas diffusion bag, the use of the gas cylinder injector system provides efficiency in sterilizing multiple lots of musical wind instruments during the sterilization cycle. In addition, the use of the high-volume exhaust ventilation system and the negative pressure created within the gas diffusion bag serve to ensure that the operator is not exposed to diffusing gas.

The sterilization of the musical wind instrument thereafter proceeds similarly to the first embodiment as illustrated in FIGS. 1 and 2, including the steps of setting the cycle times of the sterilization and purge cycles in step 280; heating the ethylene oxide gas contained in the gas diffusion bag to the sterilization temperature in step 290; maintaining the sterilization temperature to help facilitate circulation of ethylene oxide gas molecules throughout the gas diffusion bag and into the musical wind instrument contained therein in step 300; maintaining the sterilization temperature in step 310 to help facilitate diffusion of ethylene oxide gas molecules through walls of the gas diffusion bag and into the "hot" cell; exhausting ethylene oxide gas molecules that permeate through walls of the gas diffusion bag into the "hot" cell to the outside atmosphere in step 320; completing the sterilization cycle after the set cycle time in step 330; beginning the purge cycle in step 340 to exhaust residual ethylene oxide; completing the purge cycle after expiration of the set cycle time in step 350; confirming by a monitoring device or system that the sterilization parameters have been met in step 360; and, finally, removing the gas diffusion bag from the "hot" cell in step 370.

Figure 4:
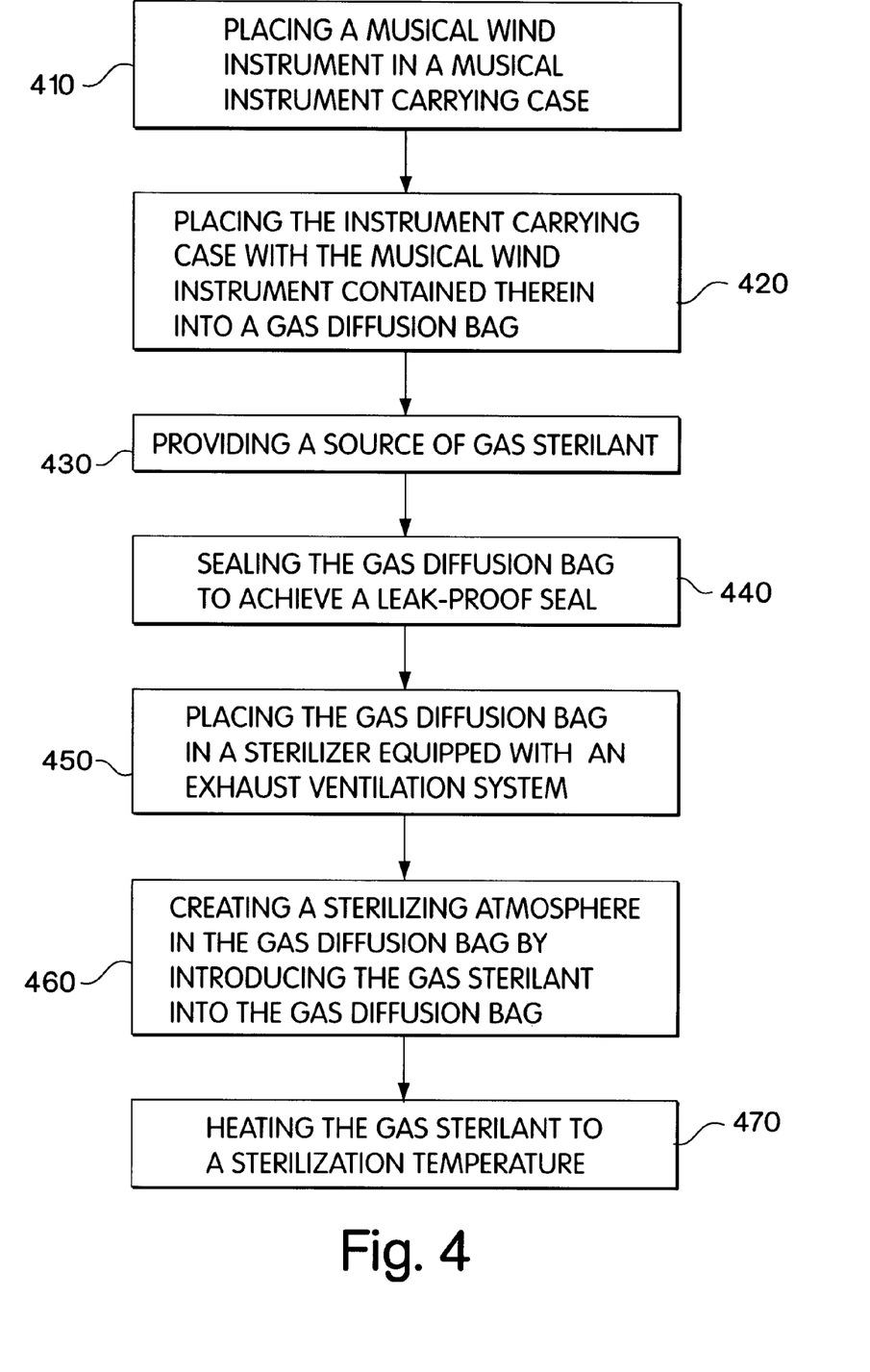
FIG. 4 is a flow diagram illustrating a third embodiment of the method of the invention.

Referring to FIG. 4, a third embodiment of the method of the invention includes sterilizing the musical wind instrument while contained in the instrument's carrying case in step 410. The carrying case containing the musical wind instrument is placed directly into the gas diffusion bag in step 420. A source of a gas sterilant is provided in step 430, such as, although not limited to, the cartridge of the first embodiment or the gas cylinder injector system of the second embodiment. The gas diffusion bag is similarly sealed as described above according to well known methods to form a substantially leak-proof seal in step 440. Thereafter, the method of sterilization of the musical wind instrument contained in the instrument's carrying case proceeds as described above in the first embodiment illustrated in FIG. 1, including the steps of placing the gas diffusion bag in a sterilizer equipped with an exhaust ventilation system in step 450; creating a sterilizing atmosphere within the gas diffusion bag by introducing the gas sterilant into the gas diffusion bag in step 460; and heating the sterilant to a set sterilization temperature in step 470. Ethylene oxide gas is capable of diffusing through walls of the instrument carrying case to circulate around and penetrate into the musical wind instrument contained therein, thereby killing microbes on substantially all surfaces of the musical wind instrument which are contacted by circulating ethylene oxide gas molecules. An advantage of this embodiment includes providing the carrying case in a sterilized state as well as the musical wind instrument to further reduce the possibility of spread of infectious microbes between end-users of the musical wind instrument.

A fourth embodiment of the method of the invention provides sterilization of musical wind instruments using standard ethylene oxide sterilizers similar to the types of sterilizers used by hospitals and laboratories for sterilization of medical instruments. For instance, AMSCO® ethylene oxide sterilizers available from Steris Corporation of Mentor, Ohio may be used to sterilize musical wind instruments. A musical wind instrument is placed in an interior of a gas diffusion bag constructed of high density polyethylene, also available from Steris Corporation. The gas diffusion bag is then placed within a sterilization chamber of the ethylene oxide sterilizer. Ethylene oxide is introduced into the sterilization chamber to create a sterilizing atmosphere, wherein ethylene oxide is heated and maintained at an appropriate sterilization temperature for an appropriate set cycle time. During the sterilization cycle, ethylene oxide gas molecules diffuse through a polyethylene membrane incorporated with a wall of the gas diffusion bag, permitting entry of ethylene oxide gas molecules into the interior of the gas diffusion bag. Ethylene oxide molecules circulate and penetrate the musical wind instrument contained within the gas diffusion bag, contacting substantially all surfaces of the musical wind instrument to achieve a sterilized condition.

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A method of sterilizing a musical instrument using a gas diffusion process, comprising steps of:

providing an open, sealable diffusion bag to contain the musical instrument;

placing the musical instrument into an interior of the open diffusion bag;

evacuating air from the diffusion bag;

sealing the diffusion bag;

positioning the diffusion bag in a chamber of a sterilizer having a ventilation system for removal of exhaust gas from the chamber;

providing a sterilizing atmosphere in the interior of the diffusion bag by releasing into the diffusion bag ethylene oxide at a concentration sufficient to act as a sterilant;

heating ethylene oxide to an appropriate temperature;

maintaining the temperature of the ethylene oxide for a sufficient time to sterilize the musical instrument; and removing the diffusion bag from the sterilizer after the musical instrument is sterilized.

2. The method of claim 1, wherein the diffusion bag is constructed of a material that allows ethylene oxide to outwardly diffuse from the diffusion bag.

3. The method of claim 1, wherein the diffusion bag is constructed of a tear-resistant material.

4. The method of claim 1, wherein the diffusion bag is constructed of low density polyethylene.

5. The method of claim 1, wherein the diffusion bag is hermetically-sealed to form a substantially leak-proof seal.

6. The method of claim 1, wherein the ethylene oxide is a unit dose measured in relation to a volume of the interior of the diffusion bag.

7. The method of claim 6, wherein the concentration of ethylene oxide is about 600 mg/l to about 750 mg/l.

8. The method of claim 1, wherein ethylene oxide is released into the diffusion bag by a delivery mechanism.

9. The method of claim 8, wherein the delivery mechanism is a cartridge containing ethylene oxide.

10. The method of claim 9, wherein the cartridge is remotely activated to release ethylene oxide.

11. The method of claim 8, wherein the delivery mechanism is a gas cylinder containing ethylene oxide with an adjustably connected injector.

12. The method of claim 1, wherein the appropriate temperature at which ethylene oxide is maintained is about 45° C. to about 55° C.

13. The method of claim 1, wherein the appropriate time at which ethylene oxide is maintained at an appropriate temperature is about 4 hours to about 16 hours.

14. The method of claim 1, further comprising a step of purging residual ethylene oxide from the diffusion bag for a sufficient time.

15. The method of claim 14, wherein the sufficient time of purging is about 16 hours to about 24 hours.

16. The method of claim 1, further comprising a step of placing the musical instrument in a musical instrument carrying case prior to the step of placing the musical instrument in the diffusion bag.

* * * * *